United States Patent
Kallmyer

(10) Patent No.: US 8,362,742 B2
(45) Date of Patent: Jan. 29, 2013

(54) METHOD AND APPARATUS FOR DYNAMIC ADJUSTMENT OF RECHARGE PARAMETERS

(75) Inventor: Todd A. Kallmyer, Tempe, AZ (US)

(73) Assignee: Medtronic, Inc., Minneapolis, MN (US)

( * ) Notice: Subject to any disclaimer, the term of this patent is extended or adjusted under 35 U.S.C. 154(b) by 284 days.

(21) Appl. No.: 12/738,065

(22) PCT Filed: Sep. 29, 2008

(86) PCT No.: PCT/US2008/078103
§ 371 (c)(1),
(2), (4) Date: Apr. 14, 2010

(87) PCT Pub. No.: WO2009/055203
PCT Pub. Date: Apr. 30, 2009

(65) Prior Publication Data
US 2010/0219796 A1    Sep. 2, 2010

Related U.S. Application Data

(60) Provisional application No. 60/982,821, filed on Oct. 26, 2007.

(51) Int. Cl.
*H02J 7/00* (2006.01)
*H02J 7/04* (2006.01)
*A61N 1/36* (2006.01)
*A61N 1/00* (2006.01)

(52) U.S. Cl. .............. 320/108; 607/29; 607/60; 607/61; 320/153; 320/162

(58) Field of Classification Search .................. 320/153, 320/108, 162; 607/29
See application file for complete search history.

(56) References Cited

U.S. PATENT DOCUMENTS

| | | | |
|---|---|---|---|
| 4,561,443 A | * | 12/1985 | Hogrefe et al. ................. 607/31 |
| 6,212,431 B1 | | 4/2001 | Hahn et al. |
| 6,441,747 B1 | * | 8/2002 | Khair et al. .............. 340/870.16 |
| 6,664,763 B2 | * | 12/2003 | Echarri et al. ................. 320/132 |
| 7,023,172 B2 | * | 4/2006 | Katou .......................... 318/807 |

(Continued)

FOREIGN PATENT DOCUMENTS
WO   WO01/83029   11/2001
WO   WO2005/037365   4/2005

(Continued)

OTHER PUBLICATIONS

PCT/US08/78103: Search Report and Written Opinion dated Sep. 29, 2008.

(Continued)

*Primary Examiner* — M'Baye Diao

(57) ABSTRACT

A recharging system and method for an implantable medical device includes: a secondary coil associated with the implantable medical device; an external power source including a primary coil and a modulation circuit operatively coupled to the primary coil, the modulation circuit being capable of driving the primary coil at a carrier frequency when the primary coil is in proximity to the secondary coil and of varying the carrier frequency in response to sensor data received from the implantable medical device; a first sensor associated with the implantable medical device and in communication with the modulation circuit, the first sensor capable of sensing a first condition indicating a need to adjust the carrier frequency during a charging process; and a second sensor associated with the implantable medical device and in communication with the modulation circuit, the second sensor capable of sensing a second condition which is affected by the carrier frequency.

18 Claims, 9 Drawing Sheets

U.S. PATENT DOCUMENTS

| | | |
|---|---|---|
| 7,167,756 B1 | 1/2007 | Torgerson et al. |
| 7,194,308 B2 * | 3/2007 | Krig et al. ........................ 607/29 |
| 7,239,918 B2 | 7/2007 | Strother et al. |
| 7,286,880 B2 | 10/2007 | Olson et al. |
| 7,286,881 B2 | 10/2007 | Schommer et al. |
| 7,715,912 B2 | 5/2010 | Rezai et al. |
| 7,774,069 B2 | 8/2010 | Olson et al. |
| 2004/0098068 A1 | 5/2004 | Carbunaru et al. |
| 2005/0075697 A1 | 4/2005 | Olson et al. |
| 2007/0156205 A1 | 7/2007 | Larson et al. |

FOREIGN PATENT DOCUMENTS

WO    WO2007/064609    6/2007

OTHER PUBLICATIONS

PCT/US08/78103: International Preliminary Report on Patentability dated May 6, 2010.

* cited by examiner

METHOD AND APPARATUS FOR DYNAMIC ADJUSTMENT OF RECHARGE PARAMETERS

FIELD OF THE INVENTION

This invention relates to implantable medical devices and, in particular, to energy transfer devices, systems and methods for implantable medical devices.

BACKGROUND OF THE INVENTION

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators and cochlear implants. Of course, it is recognized that other implantable medical devices are envisioned which utilize energy delivered or transferred from an external device.

A common element in all of these implantable medical devices is the need for electrical power in the implanted medical device. The implanted medical device requires electrical power to perform its therapeutic function whether it be driving an electrical infusion pump, providing an electrical neurostimulation pulse or providing an electrical cardiac stimulation pulse. This electrical power is derived from a power source.

In some implantable medical devices electrical power can be transcutaneously transferred through the use of inductive coupling. Such electrical power or energy can optionally be stored in a rechargeable battery. In this form, an internal power source, such as a battery, can be used for direct electrical power to the implanted medical device. When the battery has expended, or nearly expended, its capacity, the battery can be recharged transcutaneously, via inductive coupling from an external power source temporarily positioned on the surface of the skin.

While many devices and techniques have been developed to provide transcutaneous energy transfer in order to power an implantable medical device and/or charge or recharge a battery associated with an implantable medical device, external chargers associated with such devices are sometimes cumbersome and generally require the patient to take some overt step in order to associate an external charger in proximity with an internal, secondary coil associated with the implanted medical device and to initiate steps and/or procedures to accomplish a transcutaneous energy transfer in order to charge or recharge the implanted medical device. In some cases, this may require the patient to consciously remain in contact with or in the proximity of the external charging device. Such charging techniques and equipment tend to limit the flexibility and/or mobility of the patient having an implanted medical device while the device is charging.

U.S. Patent Application No. US 2003/0078634 (A1), Schulman et al, Full-Body Charger For Battery-Powered Patient Implantable Device, attempts to solve the problem of a patient having multiple implanted devices to be recharged. Schulman et al '634 discloses a full-body charger for charging one or more battery-powered devices wherein such devices are configured for implanting beneath a patient's skin for the purpose of tissue, e.g., nerve or muscle, stimulation and/or parameter monitoring and/or data communication. A support structure, typically chair-shaped or bed-shaped, capable of supporting a patient's body while providing a magnetic field to one or more of the implanted devices using one or more coils mounted within for providing power to the implanted devices. As a result, a single, generally sequential, charging cycle can charge all of the implanted devices and thus minimize the charge time requirements for a patient and accordingly improve the patient's lifestyle.

U.S. Pat. No. 6,212,430, Kung, Electromagnetic Field Source With Detection of Position of Secondary Coil In Relation To Multiple Secondary Coils, attempts to locate a secondary coil associated with a particular implanted medical device. Kung discloses an electromagnetic field source for providing electromagnetic energy to a secondary coil, including two or more primary coils that each carry a time-varying current to produce an electromagnetic field, and a controller that selectively provides current to one or more primary coils based on their position with respect to the secondary coil. The secondary coil may be implanted in a human recipient and used to provide power for the operation of a medical device, such as an artificial heart or ventricular assist device. The primary coils may be housed in furniture. For example, they may be housed in a bed mattress or mattress pad on which the recipient rests, or in a blanket for covering the recipient. The controller includes a proximity detector that identifies those primary coils that are closest to the secondary coil, and a current director that, responsive to the proximity detector, selectively direct time-varying current though the closest primary coils.

BRIEF SUMMARY OF THE INVENTION

One aspect of the invention relates to a passive recharging system for an implantable medical device which includes: a) a secondary coil associated with the implantable medical device; b) an external power source which includes a primary coil and a modulation circuit operatively coupled to the primary coil, the modulation circuit being capable of driving the primary coil at a carrier frequency when the primary coil is in proximity to the secondary coil and of varying the carrier frequency in response to sensor data received from the implantable medical device; c) a first sensor associated with the implantable medical device and in communication with the modulation circuit, the first sensor being capable of sensing a first condition indicating a need to adjust the carrier frequency during a charging process; and d) a second sensor associated with the implantable medical device and in communication with the modulation circuit, the second sensor being capable of sensing a second condition which is affected by the carrier frequency.

In another aspect, the first sensor includes a voltage sensor capable of measuring voltage across the secondary coil and the first condition is a voltage threshold.

In another aspect, the implantable medical device includes a telemetry unit which transmits sensor data from the implantable medical device to the external power source.

In another aspect, the second sensor is a temperature sensor and the second condition is a temperature at the implantable medical device.

In another aspect, the modulation circuit includes a frequency generator and a processor which is configured to control the frequency generator so as to control the carrier frequency in response to data from the voltage sensor and the temperature sensor.

In another aspect, the processor causes the frequency generator to increase carrier frequency if the voltage sensor senses a voltage lower than a predetermined voltage threshold value and the temperature sensor senses a temperature lower than a predetermined temperature threshold value.

In another aspect, the temperature threshold value is a value defined by a government regulation.

Another aspect relates to a method for charging an implantable medical device. The method includes the steps of initiating a charging process; during the charging process, monitoring a first condition of the implantable medical device; during the charging process, monitoring a second condition of the implantable medical device; and adjusting the carrier frequency if the first condition meets a first predetermined criterion and the second condition meets a second predetermined criterion.

In another aspect, the first condition is a voltage at a secondary coil within the implantable device; and the first criterion is voltage being below a voltage threshold value.

In another aspect, the second condition is a temperature at the implantable device; and the second criterion is temperature being below a temperature threshold value.

In another aspect, the second condition is a temperature at the implantable device; and the second criterion is being below a temperature threshold value.

In another aspect, the step of adjusting carrier frequency includes increasing the carrier frequency.

In another aspect, the steps of monitoring the first condition and monitoring the second condition are carried out continuously.

In another aspect, the steps of monitoring the first condition and monitoring the second condition are carried out at predefined time increments.

In another aspect, the step of adjusting the carrier frequency is carried out only if the first condition meets the first predetermined criterion and the second condition meets the second predetermined criterion.

In another aspect, the step of monitoring the first condition includes measuring a voltage across a secondary coil in the implantable medical device, and further comprising the step of comparing the measured voltage to a threshold value for voltage.

In another aspect, the step of monitoring the second condition includes measuring a temperature within the implantable medical device, and further comprising the step of comparing the measured temperature to a threshold value for temperature.

In another aspect, the method further includes the step of sensing that the implantable medical device is in proximity to an external charger; and wherein the step of initiating a charging process includes initiating a charging process in response to a determination of the implantable medical device being in proximity to the external charger.

In another aspect, the voltage threshold value is a voltage level at which energy transfer efficiency is below a desired level.

Another aspect relates to a method for charging an implantable medical device including: initiating an inductive charging process in which energy is transferred from a primary coil in an external power source to a secondary coil in the implantable medical device; during the charging process, measuring a voltage across the secondary coil of the implantable medical device; during the charging process, measuring a temperature in the implantable medical device; comparing the measured voltage to a voltage threshold value; if the measured voltage is below the voltage threshold value, comparing the measured temperature to a temperature threshold value; and if the measured temperature is below the temperature threshold value, increasing the frequency at which the primary coil is driven.

The charging system and method for charging described herein are capable of providing an inductive charging system and method suitable for use in a passive recharge system which will increase carrier frequency as needed to compensate for a voltage which would otherwise be lower than desired due to distance between the implantable medical device and the external charger, while still ensuring that the implantable medical device is not subject to excessive temperature rise.

DETAILED DESCRIPTION OF THE INVENTION

Figure 1:
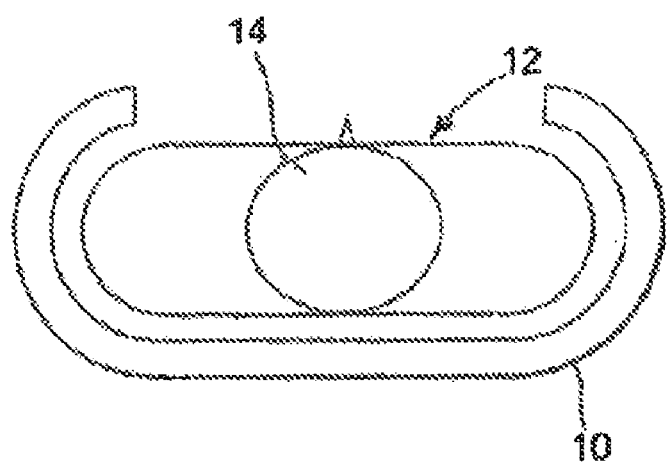
FIG. 1 illustrates a form factor for an external power source wrapping around a patient.

Passive charging or recharging refers to devices and methods that allow patients to charge or recharge implanted or external medical devices during their normal daily activities.

The passive recharging devices and methods described below allow patients to recharge their active medical devices without changing any of their daily activities. These devices may allow patients to recharge while sleeping, sitting in a chair, or walking their dog. These devices will also enable patients that would have a hard time charging a device because of its implant location to charge their devices without issues. Passive rechargers also solve the problem of frequency of patient interaction.

An external power source may be used to power or charge external or implanted medical devices placed anywhere on the body of the patient although some embodiments may be designed for specific body locations. The external power source provides form factors and other features allowing the patient to charge or recharge their medical device with no changes or minimal changes to his or her daily routines.

It is to be recognized and understood that although the focus is on passive charging that conventional charging or recharging systems, including those discussed above in the Background section of this document could be in certain circumstances, e.g., when the patient is traveling or otherwise unable to benefit from the passive system described.

In an embodiment, the external power source of the passive charging system can be semi-passive, i.e., devices and methods that fall within the normal daily activities of the patient but that, nevertheless, the patient must actively address at some level. For example, a passive charge external power source could be built into or otherwise associated with a shirt. The patient would need to wear the shirt but wearing a shirt generally would fall within normal everyday activity. Such an external charger is ambulatory and generally powered by batteries. The batteries associated with the external power source can easily be recharged conventionally by plugging into a conventional power source, plug, or by utilizing a special cradle which itself is plugged into a conventional power source. In an embodiment, the external power source is removable from the clothing, e.g., shirt, to facilitate laundry.

In general, clothes that may be used to house a passive external power source can include a vest holding an external power source for charging a medical device located in or around the area of the abdomen. A jacket may be used to charge devices located in or around the area of the abdomen or the arms. Pants may be used to charge devices located in or around the groin area or the legs. Shorts may be used to charge devices located in or around the groin area or the buttocks. An arm band may be used to charge devices located in or around the arms. A leg band may be used to charges devices located in or around the legs.

A fully passive external power source is one which the patient, caregiver or physician need only set up once and then the patient charges their medical device simply by going about their daily routine.

An automatic turn-on feature automatically senses the proximity of the medical device to the external power source or to a primary coil associated with the external power source to commence energy transfer without intervention on the part of the patient. Such proximity sensing could take the form pressure sensing, heat sensing and/or metal sensing, as examples. Of course, other proximity sensing technologies could also be utilized.

Telemetry may be used to communicate device status to an implanted medical device, particularly to determine the status of the battery of an implanted medical device. In one example, telemetry could be used to terminate energy transfer when the battery of the implanted medical device has completely charging, i.e., is full. This further allows the external power source to be fully passive, without requiring patient intervention.

Various configurations of articles to physically associate either primary coils of the external power source or the external power source itself may be used.

In an embodiment, the article could be a pad that is placed on a bed for recharge while a patient is sleeping. This pad may be a thin pad that could be placed on top of bed sheets or below the sheets. This embodiment works well for a patient with a device in their back if they sleep on their back. Patients with devices located on their side may use this embodiment if they sleep on their sides. This bed pad embodiment does not need be an ambulatory solution and could be plugged into the wall. This provides a large power source for the application and allows charging of the device at larger distances than ambulatory devices. This means that a patient that tossed or turned during the night could still be charging the device even while moving.

In an embodiment, the article could be a blanket allowing patients to recharge their device by simply placing the blanket over their device. This allows patients with devices in their extremities to recharge during sleep. It also allows patients with devices in their stomach area to recharge while sleeping on their back. The blanket could also be non-ambulatory and could be plugged into the wall for as a power source. This power source allows larger charging distances and allows the patient to move with the blanket and not worry about the loss of recharge. The passive recharge blanket could double as a heating pad by having heating wires woven through it. If the blanket were already being plugged into the wall it would be easy to use some of that power for heating the wires placed in the blanket.

In an embodiment, the article could be a pad that would rest on the back of a chair. This pad could simply be placed on the back of a patient's chair so when they were seated in that chair they would automatically be charging. The pad is especially useful for patients with devices placed in hard to reach placed in their back. The pad may be placed on the seat of the chair for charging devices placed in the buttocks or back of the leg. The pad could also be non-ambulatory allowing the power source to be from the wall. Again, this allows larger charging distances and allows the patient to move slightly during the charging session.

In an embodiment, the article could be a chair paid placed, for example, on the back of an easy chair, especially a chair routinely sat in by the patient.

In an embodiment, the article could be placed on the seat of a car routinely used by the patient.

In an embodiment, the article could take the shape of contour around the patient's body as illustrated in FIG. 1. The article is a wrap-around pad 10 at least partially encompassing the abdomen 12 of patient 14. Pad 10 could take a number of shapes to fit the contours of a patient's body. For example, pad 10 could wrap around the patient's abdomen in a 180 degree manner as shown in FIG. 1.

Figure 2:
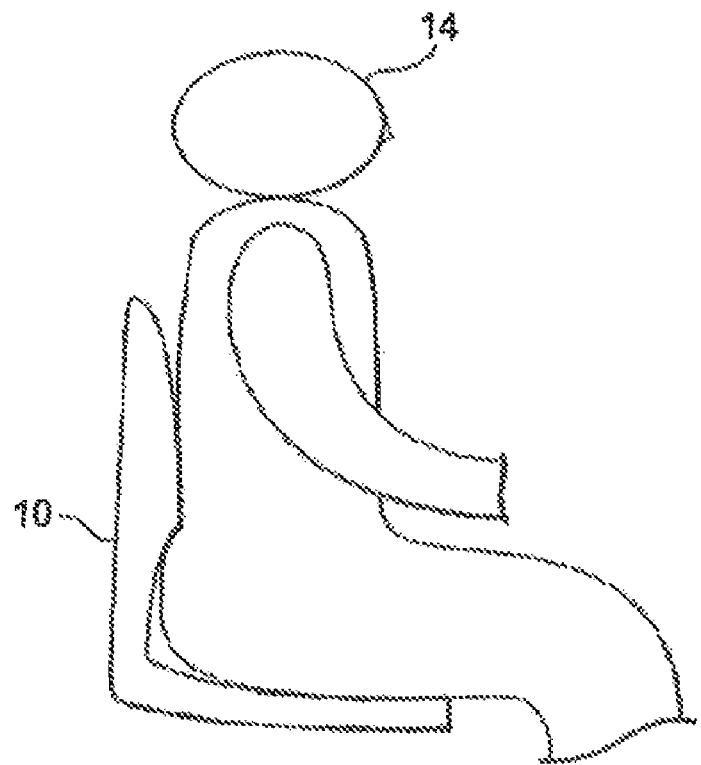
FIG. 2 illustrates a posterior shaped pad form factor for an external power source.

Alternatively, pad 10 could be designed to fit the posterior of patient 14 as illustrated in FIG. 2. In further embodiments, pad 10 could also be placed in a chair that was used by patient 14 for eating purposes. This allows patient 14 to recharge during breakfast, lunch and dinner and any other meals patient 14 might have. Still further, vibration could be included in pad 10 for comfort of patient 14. Since patient 14 generally is non-ambulatory, the power source for the vibrating feature would be from the wall and the vibration technology would be similar to that of commercially available vibrating chairs.

Figure 3:
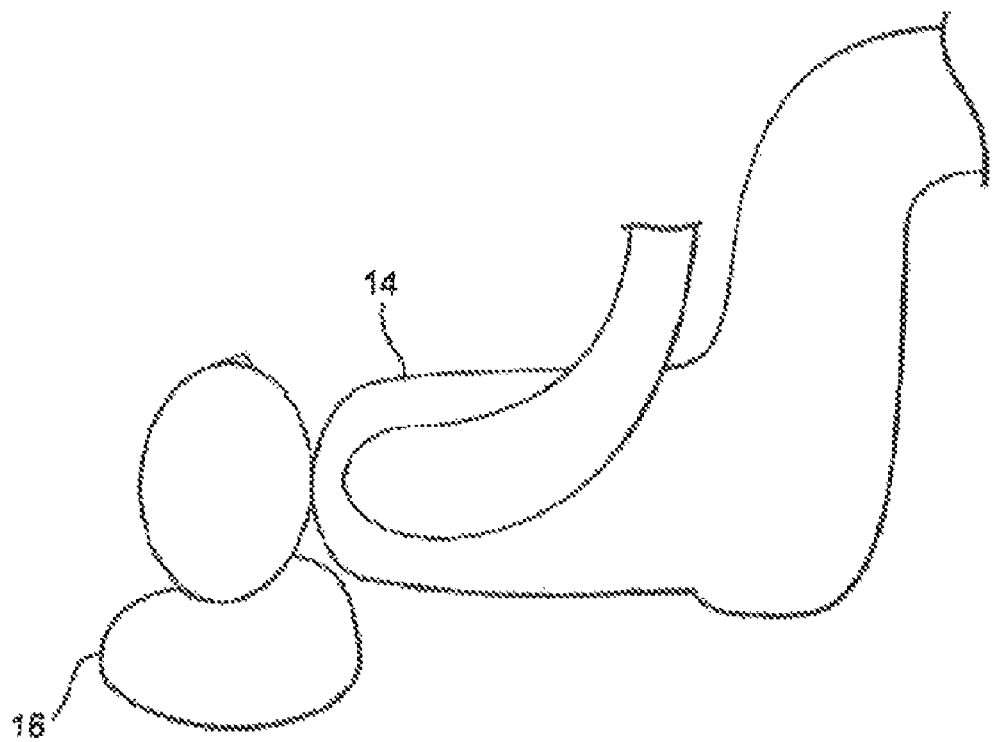
FIG. 3 illustrates a pillow form factor for an external power source.

In an embodiment, the article used for passive charging could be pillow 16 that patient 14 could rest their head on to charge or recharge as illustrated in FIG. 3. Pillow 16 allows patient 14 with a medical device placed in their head or neck to recharge passively while sleeping. Pillow 16 concept could be non-ambulatory and could be plugged into the wall. This allows significant charging distances and allows the patient to move without losing recharge.

Figure 4:
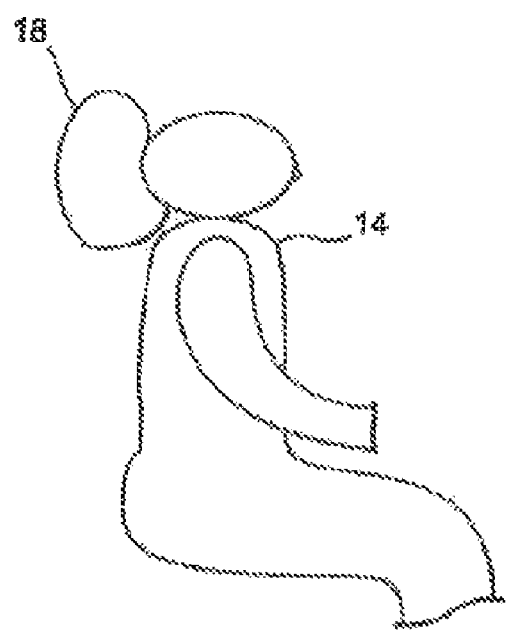
FIG. 4 illustrates a headrest form factor for an external power source.

In an embodiment, headrest 18, as illustrated in FIG. 4, could be placed on the back of a chair, on the headrest of a car seat, or any other place that patient 14 routinely rested their head. This allows patient 14 with a medical device placed in the head or neck to recharge passively while sitting upright or while lying down.

In an embodiment, passive charge or recharge could be accomplished in a recharge center for patient 14 to use in a follow-up visit to a medical clinic. There are some therapies that do not take large amounts of current and could simply be charged when patient 14 goes to a medical clinic for a follow-up appointment related to their medical device. Having passive recharge at follow-up would work well if the patient underwent routine follow-ups. Cardiac rhythm management devices such as pacemakers and defibrillators consume low amounts of current compared to neurological therapies and could have significantly lengthy recharge intervals if they were to have rechargeable batteries. This means that the patients could recharge during their follow up visit to the clinic and not need to worry about charging in between visits to the clinic.

Primary coils associated with an external power source may contain a large number of small coils interconnected and packaged in a manner that allows patient 14 to use it every day. Packaging can help prevent damage to the external power source if it is spilled on. The packaging may also make the external power more comfortable for patient 14 to be in contact with every day and may provide greater longevity of the external power source.

Packaging used with external power source could ensure that the external power source is comfortable for patient 14 to use on a daily basis. There are a number of different materials that could be used to accomplish this such as simple cotton, but there are a few materials that would be optimal for some of the form factors.

Memory foam as is widely used for commercial pillow construction would give some consistency of location of primary coils and help maintain a minimal distance between the coils (the primary coils associated with the external power source and the secondary coils associated with the medical device. Memory foam would provide a soft, comfortable covering for these coils that would have some degree of capture.

Polar fleece could be used as a blanket and for a chair paid. Polar fleece would provide a soft, warm, and comfortable covering for the blanket and chair pad. Polar fleece can also be made fairly thin which allows the distance between the primary and secondary coils to be minimized.

A breathable fabric that wicks away moisture is one embodiment covering material for the clothing form factors. An example of this material would be the material that is produced by Under Armour. This material is comfortable when worn in direct contact to the skin. By wicking away moisture from the skin this allows this material to be comfortable while in direct contact with the skin for significant periods of time.

Figure 5:
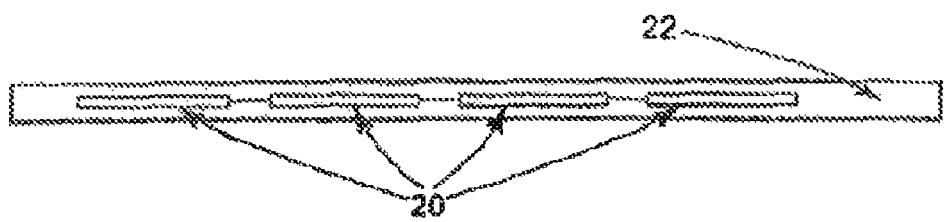
FIG. 5 illustrates a capturing of primary coils of external power source.

In certain form factors, primary coils 20 could be captured beneath a capturing material 22 to ensure that they are not damaged as illustrated in FIG. 5. This is especially the case for clothing form factors that will undergo stretching or bending forces and be more likely to get wet. Primary coils 20 could be over-molded with rubber. This would ensure flexibility but would hold primary coils 20 relative to one another. Rubber would also create a good moisture barrier to help prevent water damage to the external power source. Primary coils 20 may be packed in a gel. A gel could help the external power source form to the patient's body.

Electrical interconnect between the primary coils 20 should be able to handle significant amounts of flexing without breaking of the electrical connection. Cables of braided stranded wire could be used to interconnect primary coils 20. Braided stranded wire can handle significant amounts of flexing and provides a number of strands (so if one wire breaks there are many other wires still making the circuit). Primary coils 20 could also consist of helically wound coils that have excellent fatigue life and are used in cardiac leads that are flexed during every cardiac cycle. These primary coils 20 could be covered with some type of polymer, such as a Teflon™ type of polymer, to keep them safe. Also flex laminate substrate such as Kapton™ or FEP Teflon™ films may be used to carry traces of the interconnect material. This flexible substrate has been shown to handle many cycles of flexing and avoids or reduces damage to the interconnect.

Primary coils 20 may be of all sorts of sizes and shapes. The external power source could use a high amount of small coils. Using a high amount of small coils allows the external power source to power only a small number of coils that are directly over the medical device and allows form factors of the external power source to be highly flexible. Primary coils 20 may be 1 inch (2.54 centimeters) in diameter or less to ensure that the form factors are highly flexible.

Figure 6:
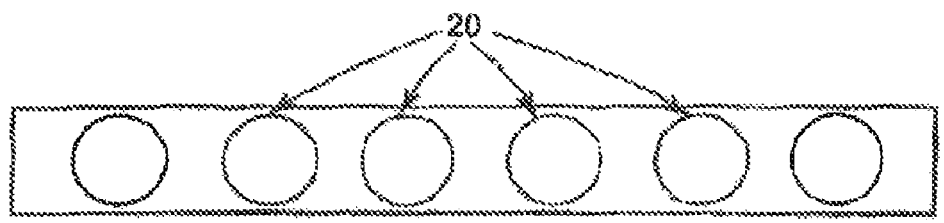
FIG. 6 illustrates an planar array of spherical primary coils.

Primary coils 20 could be shaped like spheres allowing primary coils 20 to be slightly closer to secondary coils of the medical device as shown in FIG. 6.

Figure 7:
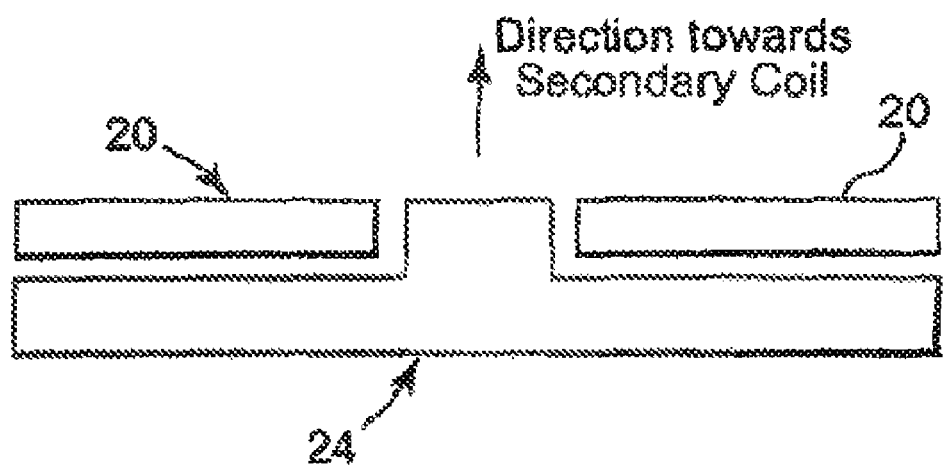
FIG. 7 illustrates use of a pot core in conjunction with a primary coil.

Pot cores 24 could be placed on the back side of each primary coil 20 to help focus the fields that are being created as illustrated in FIG. 7. Pot cores 24 could be made of materials such as manganese zinc.

Primary coils 20 could be constructed using wires having low impedance at high frequencies. For example, primary coils 20 may be constructed using Litz wire or magnet wire. This wire provides a benefit to charging because it has low impedance at high frequency. Primary coils 20 could be formed by lithography or any other etching processes. Primary coils 20 formed by lithography could be stacked and placed in series to created coils with higher numbers of turns than a single layer can provide. Primary coils 20 could be formed by pattern printing. Again, primary coils 20 formed by pattern printing could be stacked to create primary coils 20 with higher numbers of turns than a single layer can provide. Primary coils 20 may be made of a highly conductive material. Copper is an example of an inexpensive, highly conductive material. Other less conductive materials, such as MP35n may be used for better fatigue life and then can be plated with a more conductive material to bring the resistance per length down.

Figure 8:
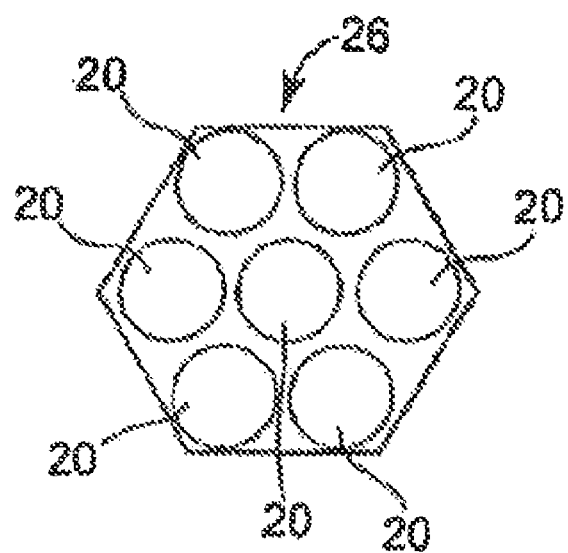
FIG. 8 illustrates a hexagonal array of primary coils.
Figure 9:
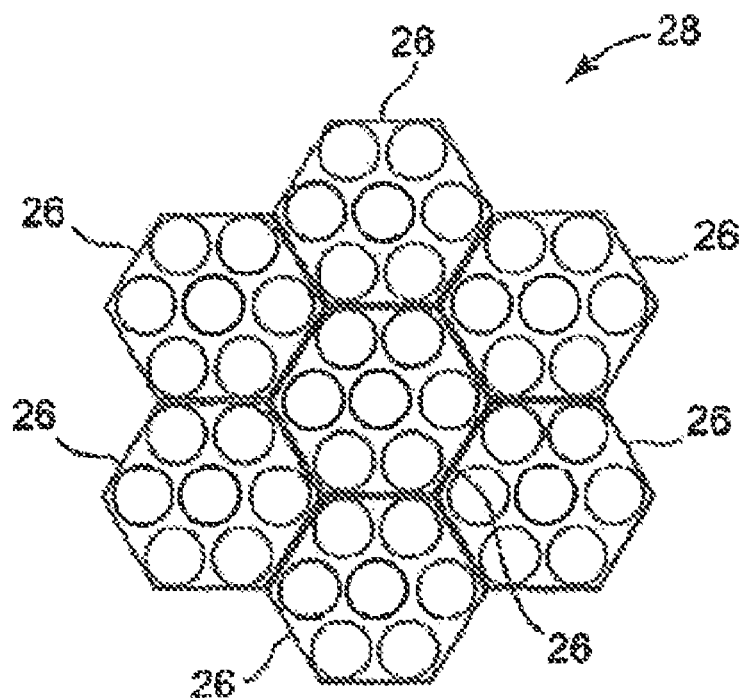
FIG. 9 illustrates a nested array of hexagonal arrays of primary coils.

Primary coils 20 may be set in a number of different configurations. First, primary coils 20 may be placed in a single plane. Primary coils could be positioned to form a hexagonal array 26 as shown in FIG. 8. Hexagonal arrays 26 may be repeated, or nested, to form an entire passive array 28 of primary coils 20 as illustrated in FIG. 9.

Figure 10:
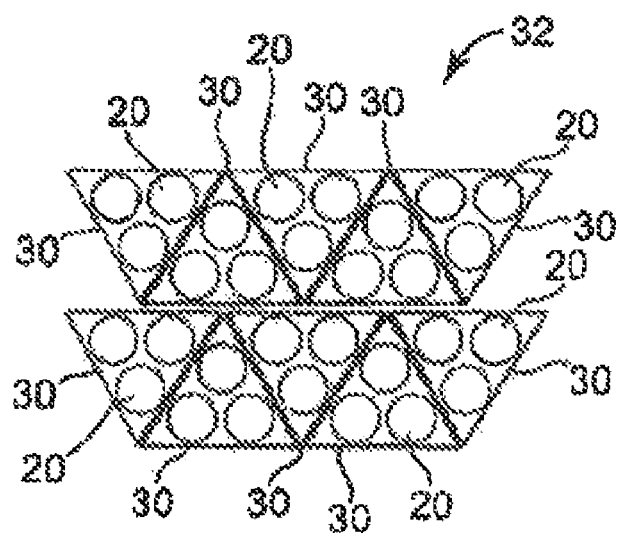
FIG. 10 illustrates a nested array of triangular arrays of primary coils.

Primary coils may be positioned in a triangular configuration whose triangles 30 may be repeated to form an array 32 of repeated triangles as illustrated in FIG. 10.

Figure 11:
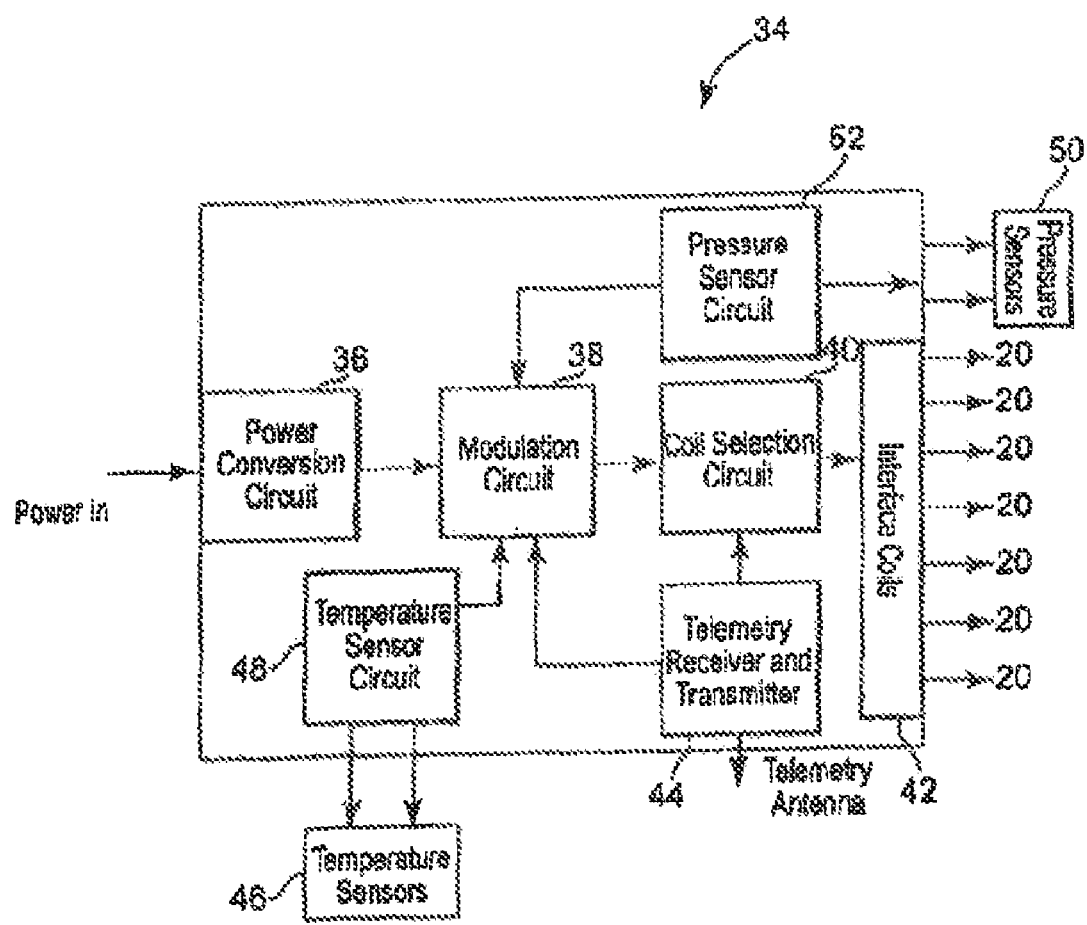
FIG. 11 is a block diagram of an external power source.

FIG. 11 illustrates a block diagram of electronics associated with the external power source 34.

External power source 34 may receive power from a wall power source or from a battery. In either case, a power conversion circuit 36 supplies appropriate power to modulation circuit 38.

The non-Ambulatory form factors (bed pad, pillow, blanket, and chair pad) allow external power source 34 to use line power. Patient 14 could simply plug external power source 34 into the wall and forget about it. Different plugs would be supplied for European patients.

The ambulatory form factors (clothes, bands) may require battery power for energy transfer. This could be accomplished using Li+rechargeable batteries. Li+batteries can be packaged in thin, flexible foil packs. These foil packs could be placed inside the ambulatory external power source 34. These batteries would have to be recharged and patient 14 could simply hang these clothes up on a special hanger to recharge them.

Modulation circuit 38 drives coil selection circuit 40 with a time-varying current enabling primary coils 20 coupled to coil selection circuit 40 through coil interface 42 to transmit energy through electromagnetic coupling.

Modulation circuit 38 is a frequency generator to generate a recharge signal, typically somewhere between 8 kiloHertz and 500 kiloHertz. The frequency of operation may depend on the form factor of external power source 34 or the variable frequency. External power source 34 could vary the frequency during a charging session to find the most optimal frequency for charging efficiency.

External power source 34 may have telemetry receiver and transmitter 44 enabling external power source 34 to in communication with an implanted medical device during a charging session. Telemetry receiver and transmitter 44 is conventional in nature and well known in the art. The implanted medical device could communicate battery status to the external power source. By knowing the battery status the external power source could stop charging when the battery of the implanted medical device was full.

It may not be possible to deliver recharge energy and telemeter to the implanted medical device at the same time so external power source 34 may have to stop sending recharge energy in order to poll the implanted medical device for information. A proximal telemetry system (5 centimeter communication distance) could be used for external power source 34 or an arm's length telemetry system could be used. Arm's length (~1 meter) telemetry can be achieved using E-field transmission (an example would be the MICS band set aside for medical device telemetry.) Arm's length telemetry (~1 meter) can also be achieved using H-field or coupled coil transmission.

External power source 34 could have an automatic turn-on sensor so patient 14 would not have to take any specific action to begin a charging session.

A temperature sensor 46 could be used to detect if patient 14 was in proximity to external power source 34. Temperature sensors 46 could be created using thermistors where the resistance changes with temperature. Temperature sensor circuit algorithm 48 receives signals from temperatures sensors 46 and alerts modulation circuit 38 to commence energy transfer upon representative of a temperature indicative of proximity of patient 14 to external power source 34 or to primary coils 20.

The charger could be automatically turned on using telemetry from the device. Telemetry could be used to automatically turn on external power source 34. External power source 34 could continuously send out requests for telemetry from the implanted medical device and when the implanted medical device was in proximity to the external power source 34, the implanted medical device would reply and external power source 34 could be turned on.

External power source 34 could include pressure sensors 50 to commence energy transfer. When patient 14 leans against a chair pad or lies down on a bed pad, pressure sensors 50 would detect the pressure. Pressure sensor circuit algorithm 52 would alert modulation circuit 38 and commence energy transfer.

Figure 12:
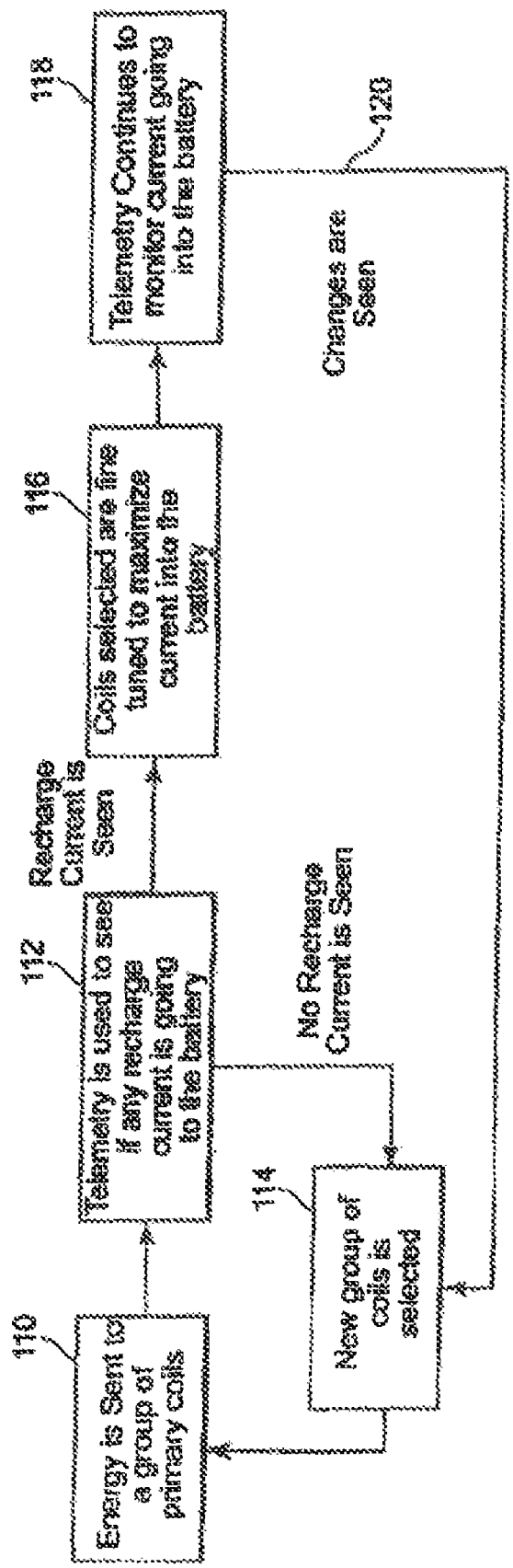
FIG. 12 is a flow chart of use of telemetry by external power source.

The implanted medical device could also communicate how much current was being put into the battery of the implanted medical device at any time. With this information, the external power source 34 could optimize the primary coils 20 that were being used to charge or the amount of power that each primary coil 20 as illustrated in FIG. 12.

Energy is sent (110) to a group of primary coils. Telemetry is used (112) to see if any charge or recharge current is going to the battery of the implanted medical device. If no recharge current is seen, a new group of primary coils 20 is selected (114) and the process returns to step 110. If recharge current is seen, primary coils 20 are fine tuned (116) to maximize current into the battery of the implanted medical device. Telemetry continues to monitor (118) current going into the battery of the implanted medical device. If changes in the current going into the battery of the implanted medical device are seen (120), a new group of primary coils 20 are selected (114) and the process repeats.

Temperature sensors 46 could also be used to ensure external power source was not getting too warm. Temperature sensors 46 could be used to detect if patient 14 was proximal to external power source 14 and could be used to monitor the temperature of external power source 14. It is generally accepted in the medical community that a temperature rise against the skin of patient 14 should not exceed 4 degrees Celsius to ensure that there is no damage to the tissue of patient 14. Temperature sensors 46 may be placed in a particular location or throughout external power source 34 to ensure that this temperature rise is not exceeded in a particular place or at any place on external power source 34.

A coil selection algorithm may be implemented in external power source 34 to help select which primary coils 20 should be powered at certain levels. It is feasible to have all of the primary coils 20 powered at all times, but selecting a certain subset of primary coils for higher power levels may increase the current delivered to the implanted medical device's battery and decrease the charging time.

Coil selection circuit 40 may use the resonant frequency of each of the primary coils 20. The resonant frequency of the primary coil 20 changes when the primary coil 20 is loaded by a secondary coil. If external power source 34 measures the resonant frequency of all of the primary coils 20 in external power source 34, external power source 34 could tell which primary coils 20 are in the closest proximity to the secondary coil. External power source 34 could then select which primary coils 20 to give the highest power.

Arm's length telemetry may also be used by coil selection circuit 40. external power source 34 could use arm's length telemetry to determine which primary coils 20 are closest to the secondary coil. External power source 34 could try powering different secondary coils 20 while communicating with the implanted medical device via arm's length telemetry to see which primary coils 20 cause the implanted medical device's battery to receive the most charge.

Short range telemetry could also be used by coil selection circuit 40 by having telemetry coils mixed in with primary coils 20 or using primary coils 20 to communicate with the implanted medical device by telemetry.

External power source 34 may automatically turn off when patient 14 has completed their charge or when patient 14 has left the proximity of external power source 34.

External power source 34 could find out when the implanted medical device's battery is full using short-range or arm's length telemetry. When the implanted medical device's battery is full it would simply send the signal via telemetry to external power source 34 that the battery was full and external power source 34 would stop transmitting recharge energy.

If external power source 34 has temperature sensors 46, external power source 34 could sense when patient 14 has left external power source 34 by looking at the temperature, typically a temperature decrease. If the temperature changes because patient 14 has left, external power source 34 could stop transmitting recharge energy.

If external power source 34 had pressure sensors 50 to check to see if patient 14 is using external power source 34, external power source 34 could sense when patient 14 left the external power source 34. When the pressure sensor 50 recognizes that patient 14 has left external power source 34, external power source 34 could stop transmitting recharge energy.

As noted above, energy transfer may cause external power source 34 to heat up. As discussed earlier, external power source 34 should preferably not have a temperature of more than four (4) degrees Celsius higher than skin of patient 14. External power source 34 may use water cooling, fan cooling, cooling with surface area radiant, refrigerator cooling or electrical cooling to ensure that external power source 34 heating is kept under control.

Figure 13:
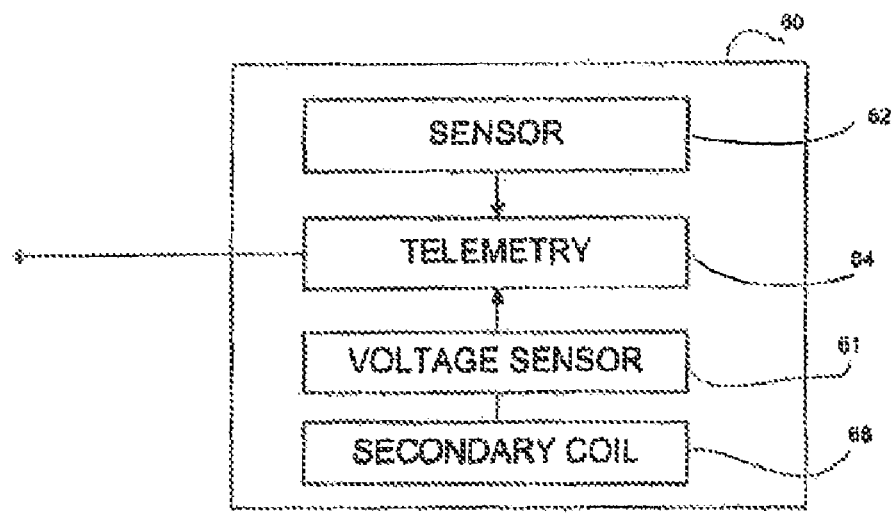
FIG. 13 is a schematic diagram showing certain elements of an implantable medical device.
Figure 14:
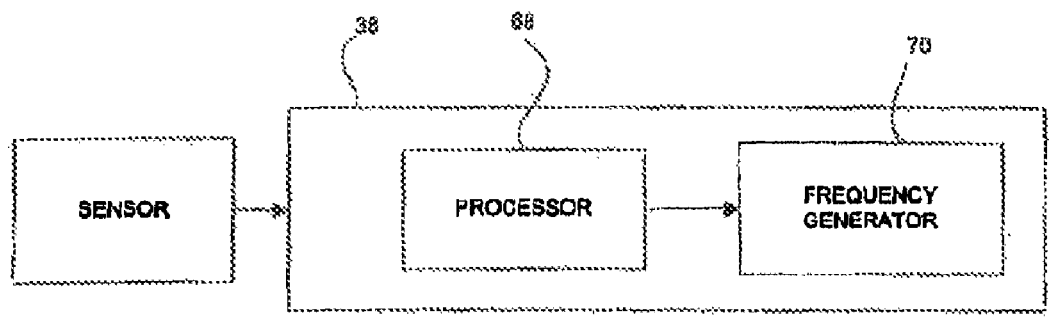
FIG. 14 is a schematic diagram of a modulation circuit.

FIG. 13 illustrates an example of an implantable medical device 60 including a sensor 62 which transmits data via a telemetry unit 64 to the external charger of FIG. 11. The implantable medical device 60 also includes the secondary coil 66. Referring to FIG. 14, the modulation circuit 38 includes a processor 68 and a frequency generator 41 controlled by the processor 68. The modulation circuit 38 is capable of driving the primary coils 20 at a variable carrier frequency. A sensor 62 of the implantable medical device 60 is in communication with the modulation circuit 38 to communicate sensed data to the modulation circuit 38.

An embodiment where the sensor 62 is capable of sensing a condition that indicates a need to adjust the carrier frequency while an inductive charging process is taking place will now be discussed. For the purposes of this discussion, a need to adjust carrier frequency encompasses a need to adjust carrier frequency in order that one or more desired or predetermined conditions are met.

An example of a condition which may indicate a need to adjust carrier frequency during the charging process is a change in distance between the secondary coil and the primary coil(s), which, if all other factors remain constant, results in a change in voltage across secondary coil and a resulting change in temperature in the implanted device. In a passive recharge system like those described above, a patient may move relative to the external power source 34 or to the primary coil(s) 20 in the external power source 24. Even when the patient remains generally in proximity to the charger, slight movements may cause the patient's implant to move relative to the primary coil(s) in a manner that changes the distance between primary and secondary coils. In a system with primary coils of about one inch diameter (2.54 centimeters), a change in distance on the order of one inch (2.54 centimeters) can have a significant effect. A change Voltage across the secondary coil increases when distance between the driven primary coil(s) and secondary coil decreases.

Carrier frequency likewise has an effect on voltage and on temperature in the implanted device. All other factors remaining constant, a higher frequency will result in a higher voltage at the secondary coil and also a higher temperature at the implanted device, since the materials commonly used in implantable medical devices, i.e., titanium, will heat up more at higher frequencies. Higher voltages across the secondary coil will generally result in higher temperature at the implantable device. Excessive heating in the implanted device is undesirable. There are generally accepted guidelines for maximum temperature for an implanted device.

There is, therefore, a trade-off between the higher voltages which can be attained at smaller distances between the primary and secondary coils due to higher efficiency of energy transfer or from higher carrier frequency, and the resultant heating of the implantable device. Since voltage and temperature are both controllable, at least in part, by adjustment of carrier frequency, the trade-off can be managed through a temperature feedback mechanism with adjustment of carrier frequency in response to temperature and voltage feedback.

In the embodiment illustrated in FIG. 13, sensor 62 is a temperature sensor. The temperature sensor 62 is located within or associated with the implantable medical device 60 to measure the temperature at the implantable device 60. A voltage sensor 61 in the implantable medical device 60 measures voltage across the secondary coil 66. Data from the temperature sensor 62 and the voltage sensor are communicated to the modulation circuit 38 via telemetry communication between the external power source 34 and the implantable medical device 60.

Examples of temperature sensors and temperature monitoring processes which may be used in these embodiments are discussed in US Published Patent Applications Nos. 2005/0075697 and 2005/0075694.

The modulating circuit 38 adjusts drive frequency as needed to achieve or maintain the desired temperature at the implantable medical device 60 while achieving or maintaining the desired voltage at the secondary coil 66. An upper temperature threshold value and a lower voltage limit are programmed into the processor 68 in the modulating circuit 38. The temperature threshold is preferably based on applicable guidelines, standards or government regulations prescribing temperature conditions for internal medical devices. Alternatively, a temperature threshold below that prescribed by regulation, standard or guideline could be chosen by a medical professional. The voltage limit is chosen as the voltage level where an increase in carrier voltage is needed to bring energy transfer up to a desired level. The processor 68 is programmed with instructions to cause the modulating circuit 38 to raise carrier frequency as needed to maintain voltage above the voltage limit so long as the temperature threshold has not been exceeded.

The threshold limits for temperature and voltage may be programmed into the processor 68 of the modulation circuit 38 during the manufacturing process. Alternatively, one or both of the temperature or voltage thresholds may be programmed in at a later time under the direction of a medical professional involved in care of the implant patient. This would be the case in an embodiment where the medical professional chooses a temperature threshold.

Figure 15:
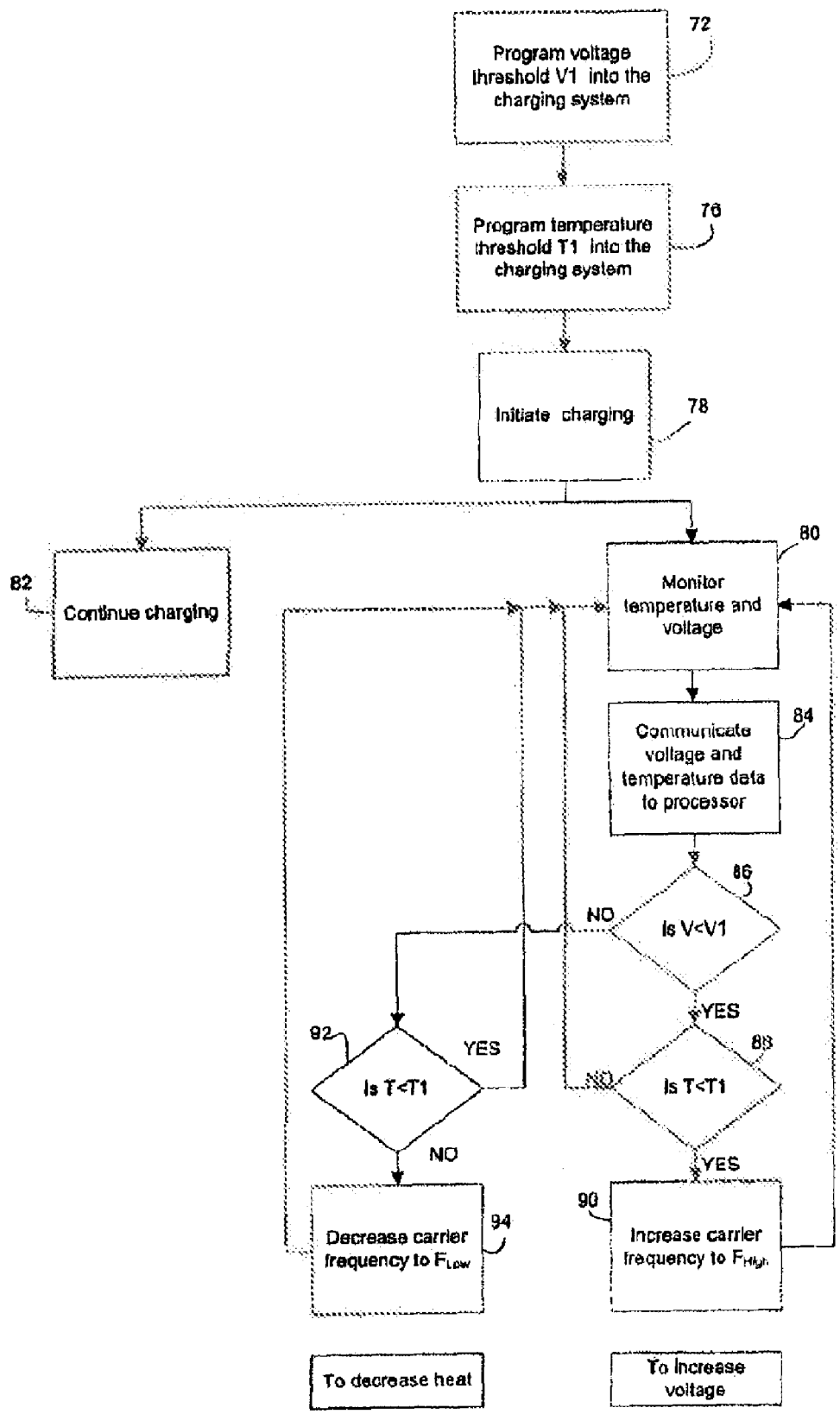
FIG. 15 is a flow chart of a temperature-based dynamic frequency adjustment process.

FIG. 15 illustrates an example of a process for temperature and voltage feedback which may be used to manage the trade-off between voltage and heating of an implantable medical device 60 which is subject to changes in the distance between the device 60 and its external charger. A voltage threshold V1 is programmed into the charging system at step 72, and a temperature threshold T1 is programmed into the charging system at step 76. These steps may be carried out simultaneously or sequentially in either order. T1 is an upper temperature limit. It may be, for example, a temperature threshold chosen in compliance with regulations or established standards for internal medical devices. V1 is a lower voltage level chosen to correspond to the point where energy transfer is inefficient to a degree which necessitates an increase in carrier frequency in order to reach an acceptable energy transfer rate.

Charging is initiated at step 78. Temperature and voltage is monitored (step 80) while charging is on-going (step 82). Temperature and voltage data is communicated to the processor in the external charger (step 84). The monitoring and the communication may be done on a continuous basis or at predefined time intervals. The processor compares the voltage to V1. (step 86). If voltage at the secondary coil is lower than V1, the processor checks device temperature to see if it is below T1 (step 88). If both conditions are met, then the carrier frequency is increased (step 90). Monitoring of the device voltage and temperature continues. If voltage is lower than V1 but device temperature is above T1, then carrier frequency is not increased. This ensures that the implantable medical device will not be excessively heated due to an increase in frequency. Temperature and voltage will continue to be monitored (80). If voltage remains below V1 but temperature decreases to a level below T1, then carrier frequency will be increased. Charging continues (82) as the monitoring, voltage and temperature comparisons and frequency adjustments take place.

If the voltage comparison at step 86 shows that voltage is higher than or equal to V1, then the processor temperature data to T1 (step 92). If temperature is greater than or equal to T1, then carrier frequency is decreased (step 94) in order to decrease heating of the implantable device. If temperature is below T1 while voltage is above or equal to V1, then carrier frequency will remain unchanged. Monitoring of voltage and temperature (80) will continue, as will charging (82).

In the illustrated process, the carrier frequency is adjustable to one of two frequencies, a low frequency $F_{low}$ (step 94) and a high frequency $F_{high}$ (step 90), depending on whether an increase or a decrease in frequency is desired. For example, these two frequencies may be set at 30 kHz and 90 kHz. Alternatively, the carrier frequency may be increased or decreased by an incremental amount which is based on actual device voltage and temperature. Using two pre-set frequencies is advantageous, however, because it significantly simplifies tuning of the charging system, compared to what would be required to tune a charging system for many different frequencies.

In this manner, a charging system is provided which will increase frequency as needed to compensate for a voltage which would otherwise be lower than desired due to distance between the implantable medical device and the external charger, while still ensuring that the implantable medical device is not subject to excessive temperature rise.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A passive recharging system for an implantable medical device comprising:
    a) a secondary coil associated with the implantable medical device;
    b) an external power source including:
        a primary coil; and
        a modulation circuit operatively coupled to said primary coil, said modulation circuit being capable of driving said primary coil at a carrier frequency when said primary coil is in proximity to said secondary coil and of varying the carrier frequency in response to sensor data received from the implantable medical device;
    c) a first sensor associated with the implantable medical device and in communication with the modulation circuit, the first sensor being capable of sensing a first condition indicating a need to adjust the carrier frequency during a charging process;
    d) a second sensor associated with the implantable medical device and in communication with the modulation circuit, the second sensor being capable of sensing a second condition which is affected by the carrier frequency.

2. The charging system of claim 1 wherein the first sensor includes a voltage sensor capable of measuring voltage across the secondary coil and the first condition is a voltage threshold.

3. The charging system of claim 2 wherein the implantable medical device includes a telemetry unit which transmits sensor data from the implantable medical device to the external power source.

4. The charging system of claim 2 wherein the second sensor is a temperature sensor and the second condition is a temperature at the implantable medical device.

5. The charging system of claim 4 wherein modulation circuit includes a frequency generator and a processor which is configured to control the frequency generator so as to control the carrier frequency in response to data from the voltage sensor and the temperature sensor.

6. The charging system of claim 5 wherein the processor causes the frequency generator to increase carrier frequency if the voltage sensor senses a voltage lower than a predetermined voltage threshold value and the temperature sensor senses a temperature lower than a predetermined temperature threshold value.

7. The charging system of claim 6 wherein the temperature threshold value is a value defined by a government regulation.

8. A method for charging an implantable medical device comprising:
    initiating a charging process by driving a primary coil of an external device at a carrier frequency, wherein the primary coil is in proximity to a secondary coil of an implantable medical device;
    during the charging process, monitoring a first condition of the implantable medical device via a first implantable sensor, wherein the first implantable sensor is capable of sensing a first condition indicating a need to adjust the carrier frequency;
    during the charging process, monitoring a second condition of the implantable medical device via a second implantable sensor, wherein the second implantable sensor is capable of sensing a second condition which is affected by the carrier frequency; and
    adjusting the carrier frequency based on data obtained via the first and second implantable sensor only if the first condition meets a first predetermined criterion and the second condition meets a second predetermined criterion.

9. The method of claim 8 wherein the first condition is a voltage at a secondary coil within the implantable device; and the first predetermined criterion is voltage being below a voltage threshold value.

10. The method of claim 8 wherein the second condition is a temperature at the implantable device; and the second predetermined criterion is temperature being below a temperature threshold value.

11. The method of claim 9 wherein the second condition is a temperature at the implantable device; and the second criterion is temperature being below a temperature threshold value.

12. The method of claim 11 wherein the step of adjusting carrier frequency includes increasing the carrier frequency.

13. The method of claim 12 wherein the steps of monitoring the first condition and monitoring the second condition are carried out continuously.

14. The method of claim 12 wherein the steps of monitoring the first condition and monitoring the second condition are carried out at predefined time increments.

15. The method of claim 11 wherein the step of monitoring the first condition includes measuring a voltage across a secondary coil in the implantable medical device, and further comprising the step of comparing the measured voltage to a threshold value for voltage.

16. The method of claim 15 wherein the step of monitoring the second condition includes measuring a temperature within the implantable medical device, and further comprising the step of comparing the measured temperature to a threshold value for temperature.

17. The method of claim 8 further comprising the step of sensing that the implantable medical device is in proximity to an external charger; and wherein the step of initiating a charging process includes initiating a charging process in response to a determination of the implantable medical device being in proximity to the external charger.

18. The method of claim 9 wherein the voltage threshold value is a voltage level at which energy transfer efficiency is below a desired level.

* * * * *